(12) United States Patent
Koo

(10) Patent No.: US 9,205,256 B2
(45) Date of Patent: Dec. 8, 2015

(54) NOCIPOINT THERAPY: THRESHOLD-GATED ELECTRICAL NEURO-IMMUNO-STIMULATION PROCEDURE

(76) Inventor: Charles C. Koo, Palo Alto, CA (US)

( * ) Notice: Subject to any disclaimer, the term of this patent is extended or adjusted under 35 U.S.C. 154(b) by 0 days.

(21) Appl. No.: 13/396,605

(22) Filed: Feb. 15, 2012

(65) Prior Publication Data

US 2012/0209348 A1     Aug. 16, 2012

Related U.S. Application Data

(60) Provisional application No. 61/443,258, filed on Feb. 16, 2011.

(51) Int. Cl.
*A61N 1/00*    (2006.01)
*A61N 1/36*    (2006.01)

(52) U.S. Cl.
CPC ................... *A61N 1/36021* (2013.01)

(58) Field of Classification Search
CPC ..................................................... A61N 1/0404
USPC ................................................. 607/46, 48, 50
See application file for complete search history.

(56) References Cited

U.S. PATENT DOCUMENTS

| | | | |
|---|---|---|---|
| 5,107,835 A * | 4/1992 | Thomas | 607/46 |
| 2003/0130706 A1* | 7/2003 | Sheffield et al. | 607/46 |
| 2010/0030299 A1* | 2/2010 | Covalin | 607/46 |

* cited by examiner

*Primary Examiner* — Christopher D Koharski
*Assistant Examiner* — Nadia A Mahmood
(74) *Attorney, Agent, or Firm* — Haverstock & Owens LLP

(57) ABSTRACT

A method of reducing pain includes first identifying a muscle; then identify a related pair of Nocipoints on the identified muscle; and applying electrical stimulation to the pair If required, the method may further comprise identifying additional pairs of Nocipoints and applying electrical stimulation to them. The stimulation should be from about 1.5 to 3.5 minutes.

29 Claims, 5 Drawing Sheets

NOCIPOINT THERAPY: THRESHOLD-GATED ELECTRICAL NEURO-IMMUNO-STIMULATION PROCEDURE

PRIORITY CLAIM

This application claims priority to and incorporates by reference U.S. Patent Application No. 61/443,258 filed Feb. 16, 2011.

FIELD OF THE INVENTION

At least one embodiment of the present invention pertains to medical procedures and more particularly, but not exclusively, to reducing pain through electrical stimulation of Nocipoints.

BACKGROUND

Chronic skeletal-muscular pain costs the US $200+B a year and increasing in terms of loss of time and medical expenses according to the 2011 CDC report. However, they are merely the manifestation of the underlying causes—skeletal-muscular injuries or pinched nerves.

Skeletal-muscular injuries from car accidents, sports, exercises, sudden movement, wrong postures or sometime unknown reasons are the major cause of such pain. Standard self-care process includes cold/heat pads and good rest for a period of time. In many cases, especially in acute cases, the body recovers; the muscle injury heals, and the pain disappears. Unfortunately, many people, 112 million in the US, get stuck with chronic pain, according to the CDC report.

Pinched nerves at spinal cord cause pain syndromes or loss of motor control at extremities (arms and legs). When a motor nerve is pinched, the patient experiences weak muscle response or even loss of motor control of the affected arm/leg. When a sensory nerve is pinched, the patient experiences tingling sensation, numbness in certain areas of the affected arm or leg. Herniated discs are often cited as the cause of the problem in radiological interpretation of CT scans. However, it is misleading because (1) most herniated discs do not even touch the nearby nerve and thus not necessarily cause any pain, and (2) herniated discs occur even in normal people with no pain or known injury. Most pinched nerve problems, as our clinical study indicates, are actually caused by injuries of the muscle groups that support and balance the spine. When the injuries of those corresponding muscles, mostly near the neck or the lower back, are healed, the pinched nerve problem and any associated pain disappear as well.

Standard treatments for chronic pain typically include physical therapy, pain medication, epidural injection of steroids, and surgeries. The treatment process is long and ineffective: Majority of the patients had little or no improvement after six months or longer of various therapies. The epidural injection is useful to reduce neural inflammation. However, most of the chronics pains described above are not neural inflammation. Thus, majority of patients either experience no improvement or temporary improvement with a rebound in a few days or few months when the epidural steroid wears off. In addition, due to the serious side-effect of steroids, epidural injection can only be used for several times. The prognosis of surgery was even less positive. Most of patients who undergo such invasive surgeries on and after six-month recovery periods found that their conditions are not better or even worse than before the surgery. Pain medications, including both prescription anti-inflammatory drugs and over-the-counter analgesic medicine, are often used to relieve the pain temporarily and reduce the inflammation hoping that the body will heal the injury itself once inflammation is reduced. For some patients with acute injury, the pain medication will bridge them through the recovery process with less or no pain. Unfortunately, chronic pain patients usually experience temporary relief with medications. The pain returns within hours after medication is taken. In essence, majority of people who have chronic pain would go through multiple years of treatments without a permanent cure.

Based on extensive medical and biological research, when deep (muscle) tissues are injured, it triggers a cascade of the healing process mediated by innate immune system: The injured muscle/soft tissue triggers the release of cytokines (chemicals carry signals to promote or inhibit immune responses), which recruit the innate immune cells (e.g., macrophages) to take away the dead and injured tissue cells. Macrophages in turn release other cytokines (e.g., IGF-1) and trigger the cascade of the muscle tissue repair and regeneration. In normal cases, the immune system eventually heals the muscle. Unfortunately, the process often gets interrupted and never completes. Interruptive processes include:

Scar tissue formation (b-FGF→fibroblast→fibrosis→scars)
Excessive and prolonged inflammation
Sheared muscle (structural damage of the connective tissue/framework)
Age effect
Cycle aborted due to various environmental influences When interrupted, the patient is stuck with the chronic pain and injury.

SUMMARY

The clinical study conducted in the application firmly implicates that nociceptors (i.e., pain receptors) of the muscle sensory nerve (esp., the C-fiber) participate (respond) in the healing process and ensure the positive signaling to the healing process and that the specific threshold-gated electrical stimulation procedure described in this application triggers the neural signaling and thus the healing process on the immune system side, based on the thousands of cases in which muscle injuries/pains recovered within a few hours to a few days after the procedure.

BRIEF DESCRIPTION OF THE DRAWINGS

One or more embodiments of the present invention are illustrated by way of example and not limitation in the figures of the accompanying drawings, in which like references indicate similar elements.

DETAILED DESCRIPTION

Figure 2:
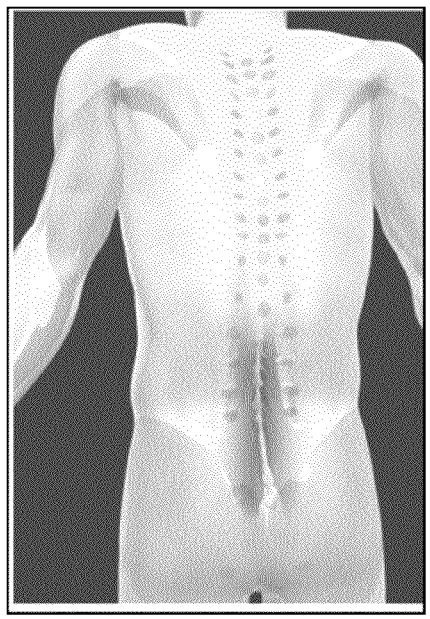
FIG. 2 illustrates locating muscle group(s) responsible for the pain of the example patient.
Figure 3:
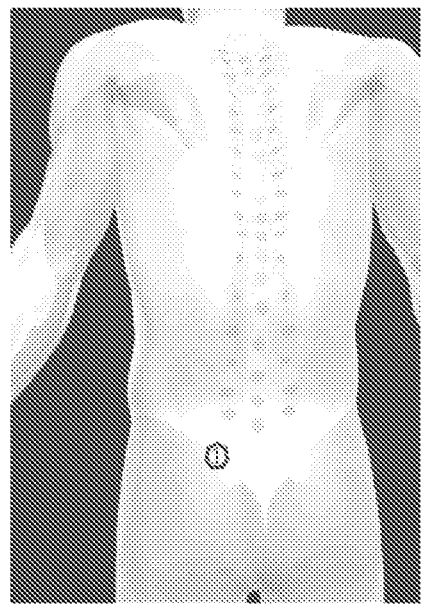
FIG. 3 illustrates an example of locating a "Nocipoint."
Figure 4:
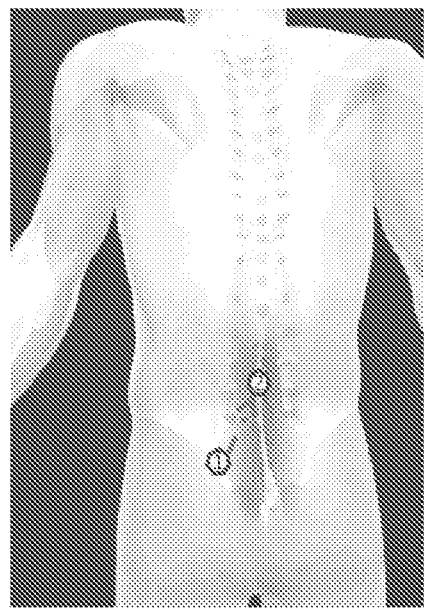
FIG. 4 illustrates tracing anatomically to find the second Nocipoint.

Nocipoint Stimulation Therapy—A Threshold-Gated Electrical Neuro-Immuno-Stimulation:

The Nocipoint Stimulation Therapy is a process using electrical stimulation in a precise manner that activates the complete healing of (1) muscle injury with associated local pain, and (2) muscle injury that causes pinched nerve and indirectly causes remote pains and/or loss of motor control at the extremities (legs, arms) in a short time:

Steps:
  (1) The patient identifies the general area of the pain: (e.g., the left shoulder/the lower left back)
  (2) Decide whether the pain is caused by the muscle(s) locally or a pinched nerve at the spinal cord remotely. In the latter case, find the muscle groups that structurally support the vertebrae near the pinched nerve. A few tests are well documented in clinical diagnosis to differentiate local muscle pain from pain/muscle weakness caused by pinched nerve. To name a few:
    a. Injury history: If someone springs his/her ankle, the ankle pain is most likely caused by local injury.
    b. The local pains are usually associated with certain movement and will always present when the same movement is performed.
    c. The pain caused by pinched nerve often can be temporarily relieved by changing the patient's posture s or via spinal traction. These maneuvers can be used to differentiate the pinched nerve problems from local muscle injuries. However, the pain will come back soon afterward.
  See FIG. 1. Example: A 59 year old patient injured his back after trying to pick up a heavy box. Couldn't bend more than 20 degrees. Had lower back pain.
  (3) Use the human anatomy to locate the muscle(s) that is likely to be responsible for the identified pain area above. This research has found that the anatomical layout of each muscle and its expected kinetics is critical in identifying the muscle. A 3-D anatomy model will be useful for this.
    See FIG. 2. Locate muscle group(s) responsible for the pain
  (4) Find the first "Nocipoint": Based on the candidate muscle group(s) identified above, press at or near one of the insertion points of the muscle(s), and find the "Nocipoint". This research has discovered that a "Nocipoint" is a small area located at the end of an injured muscle and is painful only when pressed/touched. These Nocipoints are very sensitive to even light presses, but patients usefully did not feel any pain there if not so touched. The patient will experience sharp pain when the Nocipoint is touched. Anatomically, they are where the nociceptors of the muscular sensory nerve (i.e., the free nerve ending) are.
    See FIG. 3. Example: Locate a "Nocipoint"
  (5) Find the second matching "Nocipoint" by tracing the muscle in anatomy map: For each muscular injury/pain, one will ALWAYS find another "Nocipoint" near another insertion point at the other end of the muscle. Certain muscle groups with more than two insertion points will have multiple corresponding Nocipoints. Patients are often surprised by the presence of these touch-induced pain points. Sometimes one of the Nocipoints is far away from the perceived painful area. Thus, following the muscle anatomically is critical to precisely locate the matching Nocipoints. Note that, while there may be more than two insertion points/ends of a muscle group (e.g., triceps), there are always exactly two ends of at the muscle fiber level, and thus two Nocipoints per muscle fiber.
    See FIG. 4. Trace anatomically to find the second Nocipoint The Nocipoints described here always come in pairs. No prior art has ever figured out that it requires a PAIR of the matching painful points per muscle group to induce the injury curing process.

The complexity comes in when multiple groups of muscles in the same area are injured. In such cases, multiple Nocipoints (sometimes as many as 4-6 points) may express in the nearby area and should be paired respectively based on the muscle anatomy.

(6) Nocipoint Stimulation Therapy:: In order to trigger the responses of the C-fiber nerve nociceptors, the electrical stimulation at the neuron needs to fall within a narrow range of in order to activating the neuro-immuno cascade and gain the optimal curing effect. The signaling process of the sensory nerve has the following thresholds subcutaneously:
    a. The firing threshold (when the depolarization of the neuron cell starts): 10 mV
    b. The action potential (when the depolarization ends and repolarization of the neuron cell starts): 60 mV
  Based on the biofeedback of the patients in this study, it is evident that the electrical stimulation needs to be between the two thresholds to have curing effect. However, due to the high resistance (700 K to 1.3M Ohm), the stimulating pulse at the skin surface degrades quickly before it reaches the free nerve ending of the nocireceptor. It needs to be at much higher voltage/amplitude than what is measured at the axon of the neuron. Some clinical examples of the operating stimulations at skin surface (i.e., transcutaneous electrical nerve stimulation, TENS) are as follows:

| Wave pattern | Pulse frequency | Operating range of pulse amplitude |
|---|---|---|
| Square wave/Sine wave | 9 Hz | 130 V-170 V |
| Square wave | 20 Hz | 70 V-95 V |

Note that the two transcutaneous stimulation patterns above match with the known behaviors of the spatial and temporal summation of the action potential at the sensory nerves, and typically needs a train of impulses. While the first pulse pattern has higher amplitude range, recruiting enough nerve endings to propagate the pain-signal; the second pattern works just as effective with a faster pulse (20 Hz vs. 8 Hz) yet lower amplitudes.
  Given that every person varies in age and sensitivity to pain, minor adjustments are sometimes needed: Further adjust the strength/frequency/wave pattern above the "firing potential" and within the "depolarization" range of the nociceptor. In certain embodiments, the working frequency range can be as high as about 70 Hz.
  A simple biofeedback can be used to "calibrate" the stimulation setting: when the patient starts to feel a sensation of deep pressure (i.e., when C fibers of the sensory nerve are triggered), but not a muscle spasm or sharper pain, the nociceptor is by definition above the firing potential and below the action potential thresholds. It is known that the C-fiber transmits "dull pain" or "soreness" signals (instead of the sharp pain). Thus, the patient-provided biofeedback of feeling the dull pain confirms that the electrical stimulation is within the above thresholds. That is the operating range of the Nocipoint stimulation. Note that all values above and below are approximate.

(7) For each pair of Nocipoints, carefully control the stimulation duration within a tight range between 1.5 minutes to 3.5 minutes. Minor variance is alright based on age and muscle tone, but excessive long time (e.g., >8 minutes) does not necessarily yield the best healing result. In fact, it may be counterproductive, as the clinical study revealed.

Figure 5:
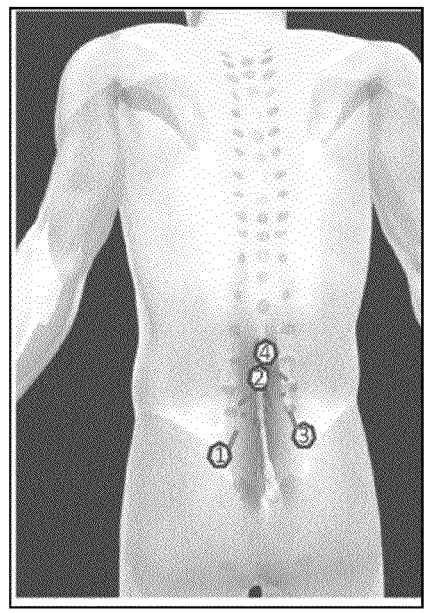
FIG. 5 illustrates an example case repeating the procedure on other pairs of Nocipoints.
Figure 6:
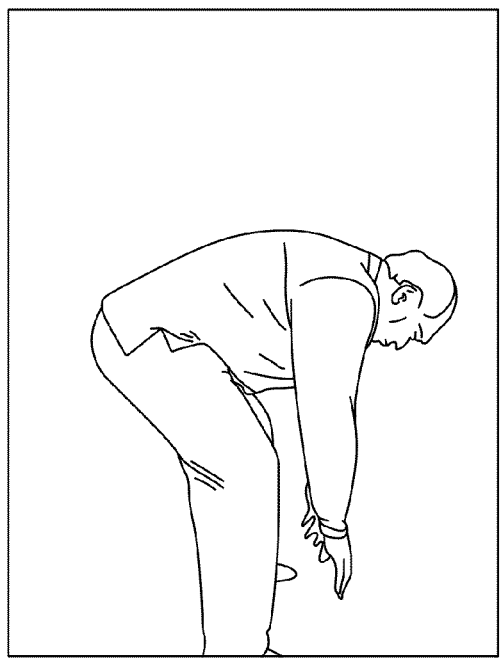
FIG. 6 illustrates within 25 minutes, the patient recovered after the first treatment with full motion range. No more back pain since then.

(8) Repeat the process on other muscle if necessary: If the correct pair of Nocipoints is stimulated, the patient will experience instant relief of pain of the stimulated muscle. And within a few minutes, the muscular function will be restored. Typically, however, multiple muscle injuries collectively cause the pain. Thus, repeat the same process to all other pairs of the Nocipoints.
See FIG. 5. Example case: Repeat the procedure on other pairs of Nocipoints (9) When all pairs of Nocipoints for the injured muscle groups are identified anatomically and stimulated, the process is complete. All pains will be relieved and patient will be able to regain all functions. Typically, it will be completed within 2-8 hours in 1-5 sessions.
See FIG. 6. Within 25 minutes, the patient recovered after the first treatment with full motion range. No more back pain since then.

(10) Waiting period: Immediately after the treatment is complete, the patient should go easy on the just-recovered muscles. Though these muscles are healed, the fibers may not be strong enough yet. To prevent new injury to the same muscle, wait for a few days. For people who are aged or weak muscles, avoid extraneous uses for at least about one week. For young people or strong muscle tone, about 2-4 days of waiting are advised. During the waiting period, some light exercise can be performed to train the newly healed muscles.

Control Study

1. Patient Profiles:
(a) Pain/tingling sensation at extremities or loss of motor control due to pinched nerves, which may or may not be present all the time. Most of them had functional deficiencies. Ages: 35-65
(b) Chronic neck pain and back pain for various (sometimes unknown) reasons, having lasted 2-20 years. All had tried many treatment protocols (physical therapy, epidural injection, acupuncture, massage, etc.) without notable improvement. Many were also on prescribed analgesics. Patients' ages are between 30 and 79.
(c) Lingering pain at extremities due to sports injuries, car accidents, or sudden movements. Many were functionally impaired for over 3 months (some multiple years). The age group: 15-68
(a) and (b) groups often had multiple areas of pain while Group (c) often had localized pain. Most of them experienced functional constraints of their arms, legs or the back. Many had symptoms from both tissue injury and pinched nerve. They were classified in either (a) or (b) for convenience. Many felt depressed, some showed allodynia or hyperalgersia. In general, these patients were all stuck with chronic pains and impaired muscular functions for a long time.

The Treatment Procedure:
The patients were given the Nocipoint Therapy: Electrically stimulate certain stimulation points that were anatomically relevant to injured tissues/sites with controlled timing, strength, dosing, etc. Because most patients had multiple problem areas, each session typically lasted for 1.5 hours.

The results (based on a study of 64 chronic pain patients):
100% patients recovered with full range of motion and only less than 10% reports Level 1 or 2 out of 10 remaining pain. 89% of patients recovered in 1-4 sessions. Full recovery is defined as (1) gaining full range of motion (age appropriate) and (2) persisting function for at least one month without recurring pains.

| Recovered in # of sessions | # of patients | percentage | Remaining pain (x/10) level when treatment stopped |
|---|---|---|---|
| 1 | 7 | 10.9% | 0-1 |
| 2 | 16 | 25.0% | 0-not noticable |
| 3 | 19 | 29.7% | 0-not noticable |
| 4 | 15 | 23.4% | not noticable-1 |
| 5+ | 7 | 10.9% | 1-2 ** |
|  | 64 | total |  |

Most patients experienced substantial or complete recovery of muscle function in the first one or two treatments. Later sessions were typically dealing with secondary/other pains that were not in the patients' chief complaint initially. (That is, when the primary problem is cured, the patient's perception starts to notice secondary and other pains.)

Arm and hand pains typically involve more muscle groups and often take longer time than neck/lower back pains.

** People who had extensive tissue damages required multiple sessions/more time to cover all the damaged tissues/muscle groups. Some patients who went through 4 or 5+ sessions stopped coming because they were happy with the substantial improvements.

Control-Test Analysis

Figure 1:
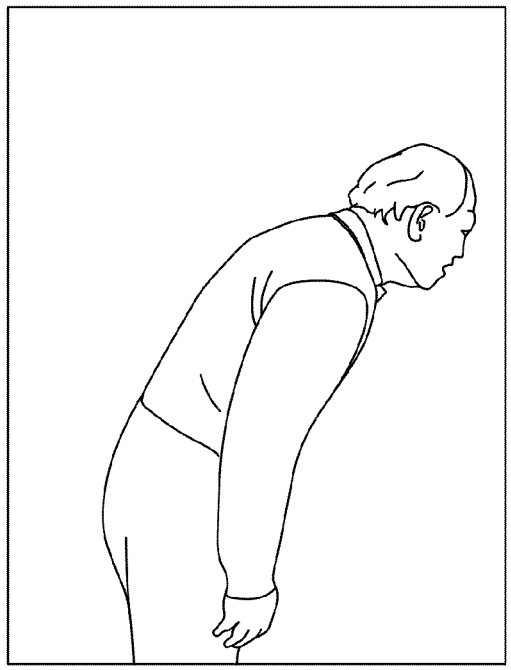
FIG. 1 illustrates a 59 year old patient injured his back after trying to pick up a heavy box. Couldn't bend more than 20 degrees. Had lower back pain.

Chronic pain patients typically have persistent pain for months or years, with other conventional treatment/therapy (See FIG. 1). The patients who received the Nocipoint Therapy experienced substantial pain relief and regained function immediately after the treatment. Unlike all prior arts, the recovery persisted. The control in this study is the historical pain level before the treatment, while the test is the pain level afterward the treatment (in the AFTER scenario).

Figure 7:
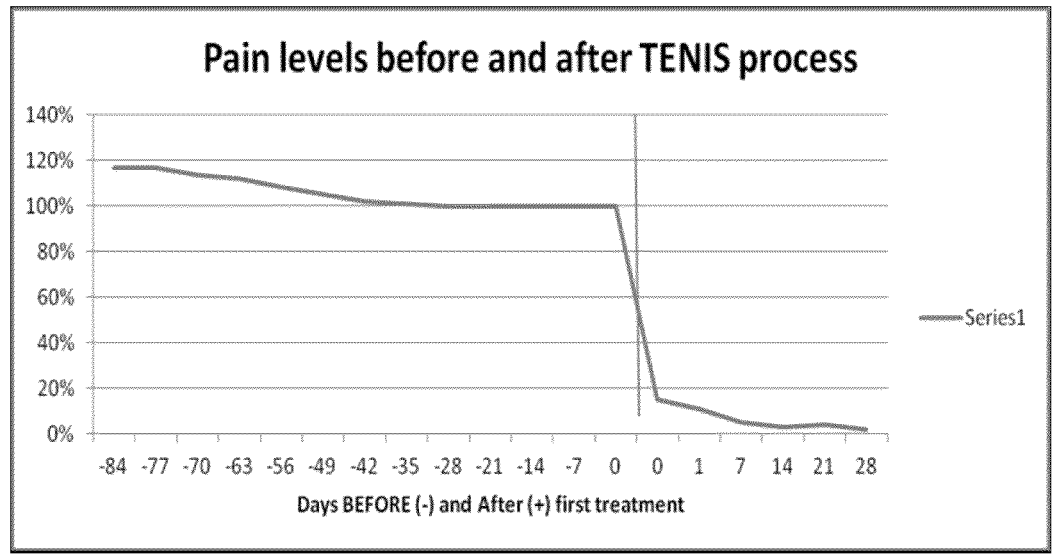
FIG. 7 is a chart illustrating relative pain levels BEFORE and AFTER the Nocipoint Therapy.

See FIG. 7. Relative pain levels BEFORE and AFTER the Nocipoint Therapy
In order to have a meaningful aggregation across all patients, the pain levels are normalized at the time right before the treatment. That is, they are defined as relative pain compared to the pain level right before the Nocipoint Therapy. Chronic pain patients typically have persistent pain for months or years, with or without conventional treatment/therapy, as indicated in the BEFORE scenario. Patients who received the Nocipoint Therapy experienced substantial pain relief and regained function soon after the treatment (the AFTER scenario). Notice that the recovery persisted afterward. (Note: history earlier than 84 days before the treatment were ignored in this chart.)

Observations:
All treatments were done within one to several hours accumulatively, spreading over one or a few sessions. The gap between sessions has minor impact on recovery, positive or negative. That is, patients technically can complete all sessions consecutively in a short period.

Patients usually experienced immediate improvement/cure when the correct Nocipoints are stimulated. This contrasts the 1-2 years of standard pain management protocol. The Nocipoint Therapy is precise, reproducible, and with near-perfect success rate.

Elimination of the placebo effect: During a session, if the points for stimulation were off by a little from the intended points mistakenly (e.g., by ½ inch), or by a lot intentionally, the patient could tell and would instantly indicate the lack of improvement. Correcting the stimulation location to the right Nocipoints will enable instant result.

After each session, the patients were instructed to go easy on exercises with the newly recovered muscles for a few days or a week for seniors, to prevent new injuries before the tissue gains enough strength.

In sum, the procedure cures pains permanently and persistently. More importantly, it heals injured tissues and restores functions. It is repeatable and the same results occur in nearly all cases.

A recent example: (with patient's permission):

The patient is 59, who injured his lower back a week before the treatment while picking up a heavy box. Had been in pain and had to roll off the bed every day. Worn waist support all days to avoid pain.

Figure 8:
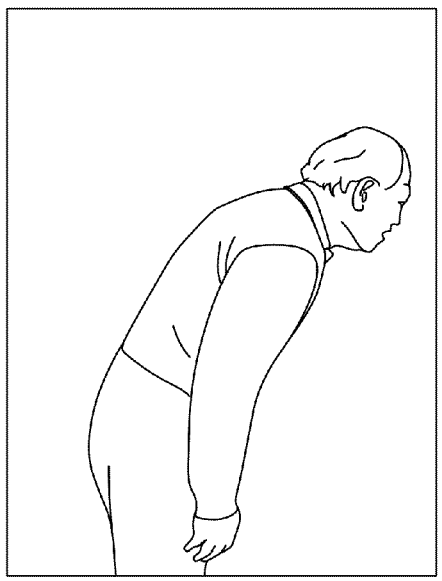
FIG. 8 illustrates a patient before treatment.

Before the treatment: See FIG. 8: the maximum angle he could bend without waist support)

Figure 9:
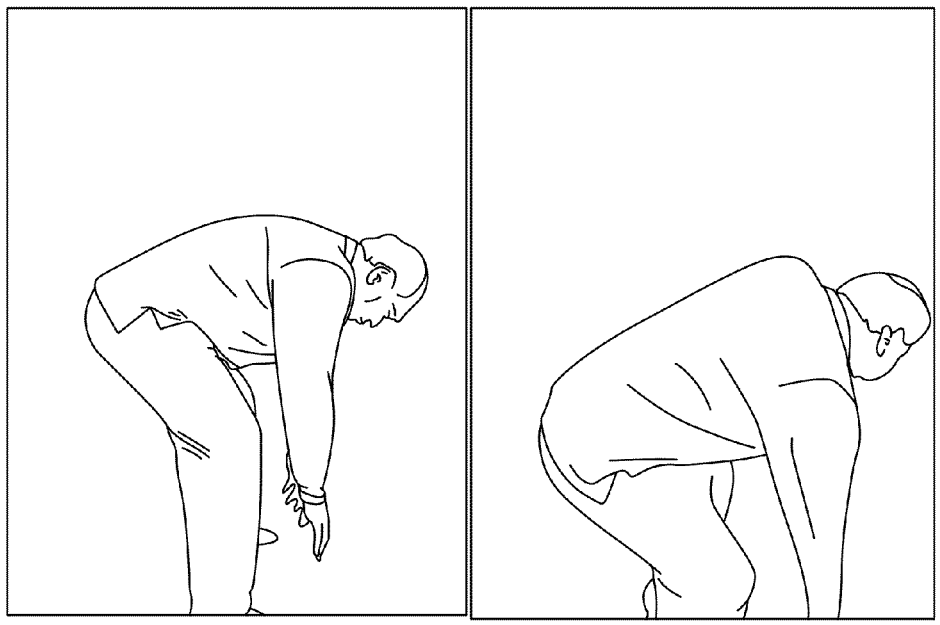
FIG. 9 illustrates the patient after treatment.

After a 25-minute treatment: Full range of motion recovered. No pain since. See FIG. 9.

Note that any and all of the embodiments described above can be combined with each other, except to the extent that it may be stated otherwise above or to the extent that any such embodiments might be mutually exclusive in function and/or structure.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

I claim:

1. A method, comprising:
   identifying an organ;
   identifying a related Nocipoint on the identified organ;
   identifying a second related Nocipoint on the identified organ;
   attaching electrodes to the pair of Nocipoints; and
   applying electrical stimulation to the pair of Nocipoints, wherein the applying electrical stimulation to the pair of Nocipoints triggers a reaction of a neuro-immuno cascade.

2. The method of claim 1, wherein the electrical stimulation for each pair of Nocipoints ranges from about 1.5 minutes to about 3.5 minutes.

3. The method of claim 1, wherein the electrical stimulation for each pair of Nocipoints has a firing minimum threshold of about 10 mV measured subcutaneously at the nerve.

4. The method of claim 1, wherein the electrical stimulation for each pair of Nocipoints has an maximum action potential of about 60 mV measured subcutaneously at the nerve.

5. The method of claim 1, wherein the electrical stimulation for each pair of Nocipoints enables a C-fiber nerve response.

6. The method of claim 1, wherein the electrical stimulation has a square wave or a sine wave pattern.

7. The method of claim 6, wherein a pulse frequency of the wave is about 20 to about 80 Hz.

8. The method of claim 7, wherein an operating range of pulse amplitude of the stimulation is about 70 to about 130 V.

9. The method of claim 7, wherein an operating range of pulse amplitude of the wave is about 130 to about 170 V.

10. The method of claim 6, wherein the electrical stimulation has a sine wave pattern.

11. The method of claim 6, wherein a pulse frequency of the square wave is about 9 Hz.

12. The method of claim 11, wherein an operating range of pulse amplitude of the square wave is about 130 to about 170 V.

13. The method of claim 1, wherein the Nocipoints include nociceptors of muscular sensory nerves.

14. The method of claim 1, wherein the applying electrical stimulation comprises a voltage within a range capable of triggering the reaction of the neuro-immuno cascade.

15. A method, comprising:
    identifying an organ;
    identifying a related Nocipoint on the identified organ;
    identifying a second related Nocipoint on the identified organ;
    attaching electrodes to the pair of Nocipoints; and
    applying electrical stimulation to the pair of Nocipoints, wherein the pair of Nocipoints are located at a muscle fiber.

16. The method of claim 15, wherein the electrical stimulation for each pair of Nocipoints ranges from about 1.5 minutes to about 3.5 minutes.

17. The method of claim 15, wherein the electrical stimulation for each pair of Nocipoints has a firing minimum threshold of about 10 mV measured subcutaneously at the nerve.

18. The method of claim 15, wherein the electrical stimulation for each pair of Nocipoints has an maximum action potential of about 60 mV measured subcutaneously at the nerve.

19. The method of claim 15, wherein the electrical stimulation for each pair of Nocipoints enables a C-fiber nerve response.

20. The method of claim 15, wherein the electrical stimulation has a square wave or a sine wave pattern.

21. The method of claim 20, wherein a pulse frequency of the wave is about 20 to about 80 Hz.

22. The method of claim 21, wherein an operating range of pulse amplitude of the stimulation is about 70 to about 130 V.

23. The method of claim 21, wherein an operating range of pulse amplitude of the wave is about 130 to about 170 V.

24. The method of claim 20, wherein the electrical stimulation has a sine wave pattern.

25. The method of claim 20, wherein a pulse frequency of the square wave is about 9 Hz.

26. The method of claim 25, wherein an operating range of pulse amplitude of the square wave is about 130 to about 170 V.

27. The method of claim 15, wherein the Nocipoints include nociceptors of muscular sensory nerves.

28. The method of claim 15, wherein the applying electrical stimulation to the pair of Nocipoints triggers a reaction of a neuro-immuno cascade.

29. The method of claim 28, wherein the applying electrical stimulation comprises a voltage within a range capable of triggering the reaction of the neuro-immuno cascade.

* * * * *